United States Patent
Jamison et al.

(10) Patent No.: US 10,012,075 B2
(45) Date of Patent: Jul. 3, 2018

(54) METHODS AND SYSTEMS FOR USING A WELL EVALUATION PILL TO CHARACTERIZE SUBTERRANEAN FORMATIONS AND FLUIDS

(71) Applicant: Halliburton Energy Services, Inc., Houston, TX (US)

(72) Inventors: Dale E. Jamison, Humble, TX (US); Michael T. Pelletier, Houston, TX (US); Ian D. Mitchell, Spring, TX (US); Mathew D. Rowe, Lafayette, LA (US)

(73) Assignee: Halliburton Energy Services, Inc., Houston, TX (US)

( * ) Notice: Subject to any disclaimer, the term of this patent is extended or adjusted under 35 U.S.C. 154(b) by 305 days.

(21) Appl. No.: 14/898,825

(22) PCT Filed: Jul. 24, 2013

(86) PCT No.: PCT/US2013/051851
§ 371 (c)(1),
(2) Date: Dec. 16, 2015

(87) PCT Pub. No.: WO2015/012823
PCT Pub. Date: Jan. 29, 2015

(65) Prior Publication Data
US 2016/0123139 A1 May 5, 2016

(51) Int. Cl.
*E21B 49/00* (2006.01)
*E21B 49/08* (2006.01)
(Continued)

(52) U.S. Cl.
CPC ............ *E21B 49/00* (2013.01); *E21B 21/067* (2013.01); *E21B 49/003* (2013.01); *E21B 49/087* (2013.01); *G01N 33/0027* (2013.01)

(58) Field of Classification Search
CPC ... G01N 33/0027; E21B 49/00; E21B 21/067; E21B 49/003; E21B 49/087
See application file for complete search history.

(56) References Cited

U.S. PATENT DOCUMENTS 5,277,263 A     1/1994   Amen
8,959,991 B2 *  2/2015   Pissarenko .......... E21B 47/1015
                                            166/252.6
(Continued)

FOREIGN PATENT DOCUMENTS

WO        2012-087175 A1     6/2012

OTHER PUBLICATIONS

International Search Report and Written Opinion issued in related PCT Application No. PCT/US2013/051851 dated Apr. 24, 2014, 14 pages.

*Primary Examiner* — Wei Wang
(74) *Attorney, Agent, or Firm* — Tenley Krueger; Baker Botts L.L.P.

(57) ABSTRACT

Systems and methods for monitoring and characterizing well bores, subterranean formations, and/or fluids in a subterranean formation using well evaluation pills are provided. In one embodiment, the methods comprise: introducing a well evaluation pill into a portion of a well bore penetrating a portion of a subterranean formation; allowing the well evaluation pill to interact with one or more components in the portion of the subterranean formation; detecting a change in the composition or properties of the well evaluation pill; and determining the presence of one or more components in the portion of the subterranean formation based at least in part on the detected change in the composition or properties of the well evaluation pill.

17 Claims, 1 Drawing Sheet

(51) Int. Cl.
*E21B 21/06* (2006.01)
*G01N 33/00* (2006.01)

(56) References Cited

U.S. PATENT DOCUMENTS

| | | |
|---|---|---|
| 2001/0036667 A1 | 11/2001 | Tayebi et al. |
| 2003/0196800 A1 | 10/2003 | Nguyen et al. |
| 2004/0094297 A1* | 5/2004 | Malone ............... E21B 47/1015 |
| | | 166/250.12 |
| 2008/0133193 A1 | 6/2008 | Gdanski et al. |
| 2014/0182844 A1* | 7/2014 | Wutherich .............. E21B 43/26 |
| | | 166/250.02 |

* cited by examiner

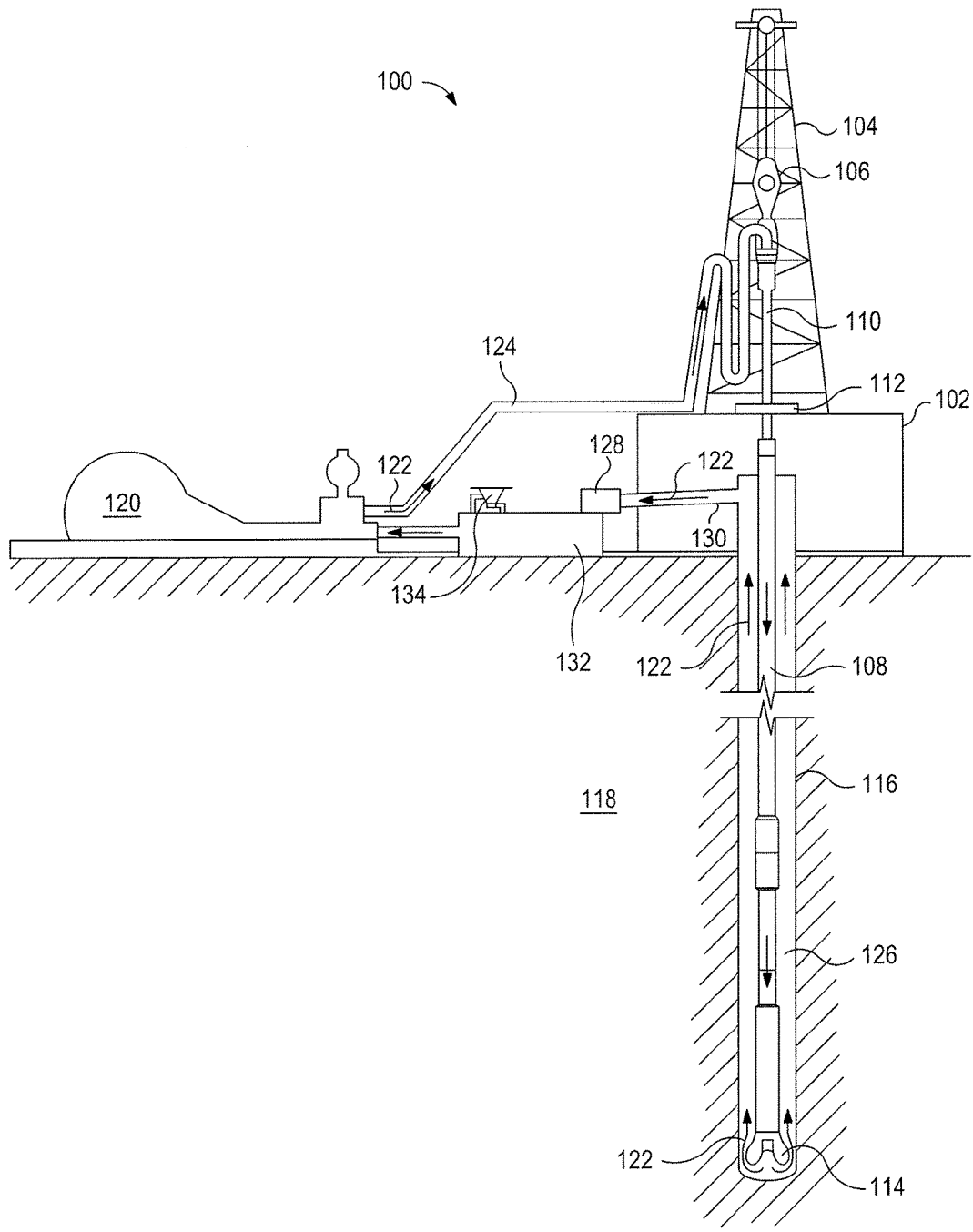

METHODS AND SYSTEMS FOR USING A WELL EVALUATION PILL TO CHARACTERIZE SUBTERRANEAN FORMATIONS AND FLUIDS

CROSS-REFERENCE TO RELATED APPLICATION

The present application is a U.S. National Stage Application of International Application No. PCT/US2013/051851 filed Jul. 24, 2013, which is incorporated herein by reference in its entirety for all purposes.

BACKGROUND

The present disclosure relates to subterranean operations and, more particularly, to systems and methods for monitoring and characterizing well bores, subterranean formations, and/or fluids in a subterranean formation.

Performance of subterranean operations entails various steps, each using a number of devices. Many subterranean operations entail introducing one or more well servicing fluids into the subterranean formation. For instance, drilling operations play an important role when developing oil, gas or water wells or when mining for minerals and the like. During the drilling operations, a drill bit passes through various layers of earth strata as it descends to a desired depth. Drilling fluids are commonly employed during the drilling operations and perform several important functions including, but not limited to, removing the cuttings from the well to the surface, controlling formation pressures, sealing permeable formations, minimizing formation damage, and cooling and lubricating the drill bit.

Properties of the drilling fluid are typically monitored during drilling operations. For instance, it is often desirable to accurately measure hydrocarbon gas concentrations of the drilling fluid as it leaves the well bore. The level of the hydrocarbon gas in the drilling fluid may affect how the well is to be drilled as well as the safety of the drilling rig and personnel involved. Moreover, the concentration of hydrocarbon gases and other components present in the drilling fluid may be indicative of the characteristics of the formation being drilled and the drilling environment. Accordingly, the analysis of drilling fluids and the changes they undergo during drilling operations may be important to the methods of drilling as well as the efficiency of the drilling operations. Consequently, during drilling, completion and testing of a well bore, it is desirable to obtain analytical measurements of the fluids that are returned to the surface from the well bore.

One method for collecting and analyzing the drilling fluid involves submerging a rotor within a vessel into the drilling fluid as the drilling fluid exits the well bore. Typically, the placement of this "gas trap" is in an open pit or header box which is exposed to atmospheric conditions. The drilling fluid is agitated as it enters into and exits out of the vessel and some of the gasses dissolved therein evaporate and escape the confines of the fluid. These vaporized gases are then collected and processed by analytical methods to determine the presence and levels of hydrocarbons and other components in the drilling fluid.

However, the usefulness and reliability of information obtained from monitoring of drilling fluids may be limited in several respects. First, many components present in the formation may not be detected in the drilling fluid if the type of drilling fluid used is not capable of absorbing or dissolving those components. The dissolution or absorption of certain components into the drilling fluid in larger quantities also may mask other components that are present in the formation in smaller quantities. Moreover, because the drilling fluid is typically circulated throughout the entire well bore, it is generally not possible to determine if a particular species is present at an interval above the bottom of the well bore.

BRIEF DESCRIPTION OF THE FIGURES

Some specific example embodiments of the disclosure may be understood by referring, in part, to the following description and the accompanying drawings.

FIG. 1 is a diagram illustrating an example of a well bore drilling assembly that may be used in accordance with certain embodiments of the present disclosure.

While the present disclosure is susceptible to various modifications and alternative forms, specific example embodiments have been shown in the figures and are herein described in more detail. It should be understood, however, that the description of specific example embodiments is not intended to limit the invention to the particular forms disclosed. On the contrary, this disclosure is to cover all modifications and equivalents as illustrated, in part, by the appended claims.

DETAILED DESCRIPTION

The present disclosure relates to subterranean operations and, more particularly, to systems and methods for monitoring and characterizing well bores, subterranean formations, and/or fluids in a subterranean formation.

The systems and methods of the present disclosure generally involve injecting or otherwise introducing into a subterranean well bore one or more pills or relatively small volume(s) of a fluid while another fluid (e.g., a well servicing fluid) is present and/or circulated in the well bore. This smaller volume of fluid is referred to herein as a "well evaluation pill". In certain embodiments, a well evaluation pill may be formulated to have a density that is higher or lower than that of the other fluid present and/or circulated in the well bore. The well evaluation pill may be formulated such that its composition or properties (e.g., chemical composition, pH, magnetic potential, optical properties, rheology, etc.) is changed when it comes into contact with certain fluids or other components in the formation by selectively interacting with one or more components that may be present in a subterranean formation. Following that interaction, the change in the composition or properties of the well evaluation pill may be detected in subsequent analysis of the well evaluation pill, for example, when the pill is circulated back to the surface. The detection of this change may indicate the presence (or absence) of one or more components in the subterranean formation. In certain embodiments, the amount of the expected change of composition or properties can be predicted based on the initial composition and/or properties of the well evaluation pill and the estimated composition of the subterranean formation and/or fluids present therein. The change of properties detected (either downhole or at the surface using one or more analytic methods) can then be compared to the expected change of properties. If the observed change in properties is the same as the expected change, then the estimated composition of the formation fluids may be confirmed. If the observed change in properties differs from the expected change, that difference may be used to more accurately predict the actual composition of the formation fluids.

The methods and well evaluation pills of the present disclosure can be used to detect any substance in a subterranean formation that will interact with a well evaluation pill. Examples of components that may be detected using a method or well evaluation pill of the present disclosure include, but are not limited to, hydrocarbons, sulfur-containing components (e.g., $H_2S$), mercury-containing components, helium (which may indicate the presence of a fault in a formation), barium, cesium, carbon dioxide (which may indicate the presence of biogenics in a formation), water, brines, tar, salt, bitumen, coal, or other minerals or ores of interest. In certain embodiments, the composition of the well evaluation pill may be formulated to facilitate capturing and/or detecting certain components in the formation. In certain embodiments, the methods and well evaluation pills of the present disclosure may be used to determine or validate, among other things, the location and/or effectiveness of various downhole operations, including but not limited to stimulation operations (e.g., fracturing, acidizing, etc.), cementing operations, and the like. In these embodiments, a well evaluation pill may allowed to interact with (e.g., flow into, penetrate, etc.) a portion of the subterranean formation where a particular operation was believed to have been performed (e.g., one or more fractures or voids in the portion of the subterranean formation that were created or enhanced during a stimulation operation). When the well evaluation pill is circulated to the surface, a change in the composition and/or properties of the well evaluation pill may be detected, which may, among other things, validate (or call into question) whether the operation was actually performed in the portion of the subterranean formation.

The methods and well evaluation pills of the present disclosure may be used to monitor or characterize fluids and/or subterranean formations in conjunction with any subterranean operation in which fluids (e.g., well servicing fluids) are present in a well bore penetrating at least a portion of a subterranean formation. In certain embodiments, the methods and well evaluation pills of the present disclosure may be used in the course of a drilling operation in which at least a portion of a well bore is drilled. In certain embodiments, the methods and well evaluation pills of the present disclosure may be used in the course of managed pressure drilling (MPD) or underbalanced drilling (UBD) operations. The systems and methods of the present disclosure also may be used during other well bore operations, including but not limited to stimulation operations (e.g., fracturing, acidizing, etc.), completion operations, remedial operations, and the like. A person of skill in the art, with the benefit of this disclosure, will recognize how to apply or implement the systems and methods of the present disclosure as disclosed herein in a particular operation.

The methods and well evaluation pills of the present disclosure are generally used in conjunction with an operation in which a well servicing fluid is circulated in a well bore penetrating at least a portion of a subterranean formation. Such well servicing fluids may comprise any fluid (liquid or gas) that is used to perform or in conjunction with an operation in a well. The well servicing fluid (e.g., drilling fluid, fracturing fluid, etc.) generally comprises a base fluid and one or more optional additives. The base fluid may comprise any fluid (e.g., liquid or gas) known in the art, such as aqueous-based fluids, non-aqueous-based fluids, gases, or any mixture thereof. Where the base fluid comprises an aqueous-based fluid, it may comprise fresh water, salt water (e.g., water containing one or more salts dissolved therein), brine (e.g., saturated salt water), or seawater. Generally, the water can be from any source, provided that it does not contain compounds that adversely affect other components of the fluid. Where the base fluid comprises a non-aqueous-based fluid, it may comprise any number of organic liquids. Examples of suitable organic liquids include, but are not limited to, mineral oils, synthetic oils, esters, and the like. In certain embodiments, the base fluid may comprise emulsions, suspensions, gels, foams, or other mixtures of fluids, solids, and/or gases. Such well servicing fluids optionally may comprise weighting agents (e.g., barites, hematite, calcium carbonates, and the like) that may be used to increase the density of the fluid. The well servicing fluid also may comprise any other additives known in the art that are suitable for a particular application of the present disclosure.

A well evaluation pill of the present disclosure comprises any base fluid known in the art, including those described in the paragraph above. In certain embodiments, the base fluid of the well evaluation pill may comprise a base fluid similar to that of the well servicing fluid present in the well bore when the well evaluation pill is introduced into the well bore. For example, if the well evaluation pill is used in conjunction with an aqueous-based drilling fluid, the well evaluation pill may comprise an aqueous base fluid. In certain embodiments, the density of the well evaluation pill may be generally slightly lower than that of the well servicing fluid. This may, among other things, allow a portion of a fluid present in a particular zone in the subterranean formation to flow into the well bore as the well evaluation pill passes that zone. This may be accomplished, inter alia, by including a lower concentration of weighting agent in the well evaluation pill, or including a lightweight additive (e.g., hollow glass microspheres, silica materials, lost circulation materials, etc.) in the well evaluation pill. In certain embodiments, such lightweight additives or weighting agents may be coated with other additives that are used to detect one or more components in the subterranean formation. A well evaluation pill of the present disclosure is usually introduced into the well bore in a relatively small volume relative to the total well bore volume. In certain embodiments, the total volume of the pill may be less than about 200 bbl. In certain embodiments, the total volume of the pill may be from about 50-100 bbl. However, the volume of a well evaluation pill of the present disclosure may be larger or smaller depending on, among other factors, the length of the interval of interest in the well bore, the geometry of the well bore, the type of components in the formation being detected, the flow rate of the pill through the well bore, the expected rate of reaction between the pill and a component in the formation, and the like. A person of skill in the art, with the benefit of this disclosure, will be able to select the appropriate pill volume for a particular application.

In certain embodiments, the entire volume of the well evaluation pill may be introduced into and/or circulated in the well bore in a single discrete interval such that it does not significantly mix with a well servicing fluid in the well bore. In these embodiments, one or more additional pills, spacers, or other fluids may be introduced into the well bore before and/or after the well evaluation pill, among other reasons, to help isolate the well evaluation pill from other fluids and/or pills in the well bore. In other embodiments, certain amounts of the well evaluation pill may be permitted mix or intermingle with one or more well servicing fluids in the well bore as it is circulated therein.

The physical properties and/or composition of a well evaluation pill of the present disclosure may be formulated to selectively facilitate interaction with one or more components to be detected in the subterranean formation. For example, the well evaluation pill may be formulated to chemically react with, dissolve, absorb, and/or otherwise capture one or more selected components in the formation (while not doing so with other components in the formation) when the well evaluation pill comes into contact or communication with those components. These interactions produce one or more detectable changes in composition or other properties of the well evaluation pill and/or the well servicing fluid. For example, the well evaluation pill may contain a solvent in which the component being detected is soluble. The component may be removed from solution and/or detected in the well evaluation pill when the well evaluation pill is circulated to the surface. Another embodiment of a well evaluation pill of the present disclosure may comprise iron oxide in an amount sufficient to interact with sulfur components (e.g., $H_2S$, CSO, $SO_2$, $CS_2$) present in a subterranean formation. The reaction between the iron oxide and sulfur components may produce iron sulfate, which may be detected in the well evaluation pill using any number of conventional analytical methods. In another embodiment, the well evaluation pill may comprise one or more ion-exchange resins (e.g., thiol-based resins) that are capable of complexing with mercury or sulfur components in the subterranean formation that subsequently may be detected in the ion exchange resin, for example, once the well evaluation pill containing those resins has been circulated to the surface.

In certain embodiments, the well evaluation pill may be formulated to alter the rheological properties of a particular fluid in the subterranean formation, which may, among other effects, increase the rate at which that fluid flows into the well bore. In certain embodiments, the rheological properties (e.g., viscosity, gel strength, yield point, etc.) of the well evaluation pill also may be selected and/or altered in order to facilitate the interaction between the well evaluation pill and a component in the formation, for example, in order to control the rate of any reaction with components in the formation. In certain embodiments, the known composition of the well evaluation pill (in combination with the flow rate of the pill in the well bore and other known conditions in the well bore such as temperature, pressure, etc.) may be used to calculate the amount of the component in the subterranean formation based on the amount of the component or other reaction by-product detected in the well evaluation pill after its circulation in the well bore.

The methods of the present disclosure generally comprise introducing a well evaluation pill into a well bore penetrating at least a portion of a subterranean formation, allowing the well evaluation pill to interact with one or more components in a subterranean formation, and detecting a change in the composition and/or properties of the well evaluation pill, the change indicating the presence and/or amount of the one or more components in the subterranean formation. In the course of a given operation, any number of well evaluation pills may be introduced into a particular well bore. In certain embodiments, one may introduce a separate well evaluation pill for each distinct zone of a subterranean formation that is detected to have different composition or other properties. This may be determined as a well bore is drilled through those different zones, in advance of the drilling operation, or after the drilling operation has been completed.

The methods and well evaluation pills of the present disclosure may be used to monitor and/or detect components in any zone of the subterranean formation penetrated by the well bore by directing the well evaluation pill to the desired interval of the well bore. This may be accomplished using a number of techniques and equipment known in the art. For example, in the course of a drilling operation, if the zone of interest of the subterranean formation of interest is located some distance above the bottom of the well bore, the drillstring may be lifted such that drill bit is adjacent to the zone of interest, and the well evaluation pill can be pumped through the drillstring to that location. In other embodiments, isolation techniques such as plugs, packers, diverting fluids, and the like may be used to isolate the interval near the zone of interest before the well evaluation pill is introduced. In certain embodiments, one or more well servicing fluids (e.g., drilling fluids, spacer fluids, etc.) may be pumped or otherwise introduced into the well bore behind the well evaluation pill to displace the well evaluation pill into a selected interval in the well bore.

When the well evaluation pill passes the selected portion of the subterranean formation, fluids present in that area may flow into the well bore and interact with the well evaluation pill. The rate at which the well evaluation pill and/or other fluids are pumped or introduced into the well bore may depend on, among other things, the rate of reaction between the well evaluation pill and selected components in the well bore, the densities of various fluids in the well bore, and the like. In certain embodiments, an additional pill having a density higher or lower than that of the fluid present in the well bore (e.g., the well servicing fluid) may be introduced into the well bore before and/or after the well evaluation pill, among other purposes, to balance a pressure change created by the well evaluation pill.

Once the well evaluation pill has passed the selected portion of the subterranean formation, the change in the composition and/or properties of the well evaluation pill may be detected at any point thereafter. In certain embodiments, a change in the composition and/or properties of the well evaluation pill may be detected while the well evaluation pill is still in the well bore, for example, using one or more downhole sensors (e.g., optical sensors, pH sensors, etc) disposed in the well bore. In other embodiments, the well evaluation pill (and other fluids in the well bore) may be circulated to the surface where the composition and/or properties of the well evaluation pill can be analyzed from a sample of the well evaluation pill. In certain embodiments, the methods of the present disclosure may include a step in which the well evaluation pill is separated from other fluids when the well evaluation pill is detected in the fluids circulated out of the well bore. These separation and detection steps may be accomplished using any means known in the art, including but not limited to flow diversion methods, gravity separation methods, heating separation methods, shakers, liquid extractor separators, and the like.

The composition and/or properties of the well evaluation pill may be analyzed using any means or apparatus known in the art. In certain embodiments, the well evaluation pill may be inspected visually to detect color changes that result from the interaction of the well evaluation pill and one or more components in the formation. In other embodiments, a sample of the well evaluation pill may be analyzed using one or more analytical methods known in the art, including but not limited to, optical spectroscopy, gas chromatography, mass spectrometry, liquid chromatography (e.g., HPLC), solid state analytical methods, or any combination thereof (e.g., GCMS). In certain embodiments, the analysis of the composition and/or properties of the well evaluation pill may be conducted substantially simultaneously as the well evaluation pill interacts with one or more components in the subterranean formation and/or as the well evaluation pill is circulated out of the well bore (i.e., substantially in or near real time). In other embodiments, the analysis of the composition and/or properties of the well evaluation pill may be conducted at a point in time after downhole operations have been completed.

In certain embodiments, systems and method of the present disclosure may utilize gas extraction system to extract a gaseous sample from the well evaluation pill for analysis, which may comprise any system known in the art that is capable of performing that function. The extraction system may include a fluid gas extraction system for extracting any gases dissolved in the fluid. In one exemplary embodiment, the fluid gas extraction system may be the EAGLE™ or CVE™ gas extraction systems available from Halliburton Energy Services of Duncan, Okla. The extraction system may liberate and extract dissolved gases from the well evaluation pill in a controlled manner. The collected gases may then be directed to a gaseous sample outlet and delivered to an one or an array of analyzers for processing. In one embodiment, the extraction system may include one or more pumps for transporting the well evaluation pill sample (and, optionally, drilling fluid samples) through the extraction process and returning the drilling fluid sample to the rig at the outlet of the extraction system. The extraction system may further include a heater for regulating the temperature of the sample and a degasser for providing a sealed method of liberating and separating dissolved gases from the sample and collecting these gasses for analysis while displacing the spent liquid to be returned to the rig through the outlet. The extraction system may further include a cooler for cooling the sample gas prior to analysis and sensors that allow the process to be continuously measured. The operations of the extraction system are well known to one of ordinary skill in the art and will therefore not be discussed in detail herein.

A gas analyzer may be coupled to the gas extraction system, integrally formed with the extraction system, or may be located in another place, building, unit or work area, separate from the extraction system. In this embodiment, the gas extracted from the fluid by the extraction system may be directed to a gas analyzer through a gaseous sample outlet. Gas analyzers are well known to those of ordinary skill in the art and will therefore not be discussed in detail herein. The gas analyzers may be used to analyze the gas sample extracted from the well evaluation pill sample and, in particular, detect species present therein (e.g., compounds that were present in the formation, or products of any chemical reaction that occurred between the well evaluation pill and such components).

In certain embodiments, one or more fluid measurement devices that are configured to detect volumes and/or flow rates of one or more fluids or pills (e.g., the well evaluation pill) introduced into or exiting the well bore may be positioned along one or more of the fluid lines feeding one or more fluids (e.g., drilling fluids) and/or pills into the well bore. These fluid measurement devices may comprise any type of sensor device known in the art capable of monitoring fluid volume or flow, including but not limited to acoustic sensors, nuclear sensors, coriolis meters, doppler radar, vortex flow meters or sensors, calorimetric flow meters or sensors, magnetic flow meters or sensors, electromagnetic meters or sensors, differential pressure meters or sensors, open channel meters or sensors, and the like. These fluid measurement devices may be communicatively coupled to a control system and/or information handling system that, among other things, uses data from those sensors to perform calculations in the methods of the present disclosure as described below.

In certain embodiments, a control system may be used to collect, process and display data regarding activities at the well site (either automatically via sensors at the well site or manually entered into the system), perform calculations using that data, as described above, and/or execute instructions to perform various functions at a well site. The control system may comprise an information handling system, such as a programmable logic controller or PLC, a suitably programmed computer, etc. Any suitable processing application software package may be used by the control system to process the data. In one embodiment, the software produces data that may be presented to the operation personnel in a variety of visual display presentations such as a display. In certain example system, the measured value set of parameters, the expected value set of parameters, or both may be displayed to the operator using the display. For example, the measured-value set of parameters may be juxtaposed to the expected-value set of parameters using the display, allowing the user to manually identify, characterize, or locate a downhole condition. The sets may be presented to the user in a graphical format (e.g., a chart) or in a textual format (e.g., a table of values). In another example system, the display may show warnings or other information to the operator when the central monitoring system detects a downhole condition. Suitable control systems and interfaces for use in the methods and systems of the present disclosure may comprise SENTRY™ and INSITE™ provided by Halliburton Energy Services, Inc. Any suitable control system or interface may be used in keeping with the principles of this disclosure.

In certain embodiments, the control system may be communicatively coupled to an external communications interface. The external communications interface may permit the data from the control system to be remotely accessible (i.e., from a location other than the well site) by any remote information handling system communicatively coupled to the external communications interface via, for example, a satellite, a modem or wireless connections. In one embodiment, the external communications interface may include a router.

In accordance with certain embodiments of the present disclosure, once feeds from one or more sensors are obtained, they may be combined and used to identify various metrics. For instance, if there is data that deviates from normal expectancy at the rig site, the combined system may show another reading of the data from another sensor that may help identify the type of deviation. As would be appreciated by those of ordinary skill in the art, with the benefit of this disclosure, a control system may also collect data from multiple rigsites and wells to perform quality checks across a plurality of rigs.

As would be appreciated by those of ordinary skill in the art, with the benefit of this disclosure, one or more information handling systems may be used to implement the methods disclosed herein. In certain embodiments, the different information handling systems may be communicatively coupled through a wired or wireless system to facilitate data transmission between the different subsystems. Moreover, each information handling system may include a computer readable media to store data generated by the subsystem as well as preset job performance requirements and standards.

Among the many advantages and benefits provided by the methods, systems, and well evaluation pills of the present disclosure, in certain embodiments, these methods, systems, and well evaluation pills may provide more accurate and/or reliable characterization of fluids and or other components present in a subterranean formation. For example, the change in conditions produced by a pill of a known composition provides another data point that can be used to verify and/or calculate characteristics of a formation independent of a steady-state analysis of drilling fluids. The use of a selectively-formulated well evaluation pill also may provide increased accuracy by screening out other variables that could otherwise skew the direct measurement or observation of that component. The methods and systems of the present disclosure also enable more localized analysis of a particular zone of interest in a subterranean formation penetrated by a well bore, which may allow operators to more narrowly identify the location in a subterranean formation in which selected components (e.g., hydrocarbons) reside. In certain embodiments, information regarding various components and phenomena (e.g., faults, environmental hazards, washouts, and the like) in the formation may be obtained in or near real-time in the course of drilling operations. This information may, among other benefits, allow operators to identify problems in during downhole operations and/or take measures to optimize those operations while in progress, thereby increasing the efficiency with which those operations can be conducted.

For purposes of this disclosure, an information handling system may include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, an information handling system may be a personal computer or tablet device, a cellular telephone, a network storage device, or any other suitable device and may vary in size, shape, performance, functionality, and price. The information handling system may include random access memory (RAM), one or more processing resources such as a central processing unit (CPU) or hardware or software control logic, ROM, and/or other types of nonvolatile memory. Additional components of the information handling system may include one or more disk drives, one or more network ports for communication with external devices as well as various input and output (I/O) devices, such as a keyboard, a mouse, and a video display. The information handling system may also include one or more buses operable to transmit communications between the various hardware components.

For the purposes of this disclosure, computer-readable media may include any instrumentality or aggregation of instrumentalities that may retain data and/or instructions for a period of time. Computer-readable media may include, for example, without limitation, storage media such as a direct access storage device (e.g., a hard disk drive or floppy disk drive), a sequential access storage device (e.g., a tape disk drive), compact disk, CD-ROM, DVD, RAM, ROM, electrically erasable programmable read-only memory (EEPROM), and/or flash memory; as well as communications media such wires, optical fibers, microwaves, radio waves, and other electromagnetic and/or optical carriers; and/or any combination of the foregoing.

The terms "couple" or "couples," as used herein are intended to mean either an indirect or a direct connection. Thus, if a first device couples to a second device, that connection may be through a direct connection, or through an indirect electrical connection via other devices and connections. The term "communicatively coupled" as used herein is intended to mean coupling of components in a way to permit communication of information therebetween. Two components may be communicatively coupled through a wired or wireless communication network, including but not limited to Ethernet, LAN, fiber optics, radio, microwaves, satellite, and the like. Operation and use of such communication networks is well known to those of ordinary skill in the art and will, therefore, not be discussed in detail herein.

It will be understood that the term "oil well drilling equipment" or "oil well drilling system" is not intended to limit the use of the equipment and processes described with those terms to drilling an oil well. The terms also encompass drilling natural gas wells or hydrocarbon wells in general. Further, such wells can be used for production, monitoring, or injection in relation to the recovery of hydrocarbons or other materials from the subsurface. This could also include geothermal wells intended to provide a source of heat energy instead of hydrocarbons.

The exemplary well evaluation pills, methods, and systems disclosed herein may directly or indirectly affect one or more components or pieces of equipment associated with the preparation, delivery, recapture, recycling, reuse, and/or disposal of the disclosed fluids and additives. For example, and with reference to FIG. 1, the disclosed well evaluation pills, methods, and systems may directly or indirectly affect one or more components or pieces of equipment associated with an exemplary well bore drilling assembly 100, according to one or more embodiments. It should be noted that while FIG. 1 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling assembly 100 may include a drilling platform 102 that supports a derrick 104 having a traveling block 106 for raising and lowering a drill string 108. The drill string 108 may include, but is not limited to, drill pipe and coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 from the well surface. As the bit 114 rotates, it creates a borehole 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the borehole 116. At the surface, the recirculated or spent drilling fluid 122 exits the annulus 126 and may be conveyed to one or more fluid processing unit(s) 128 via an interconnecting flow line 130. After passing through the fluid processing unit(s) 128, a "cleaned" drilling fluid 122 is deposited into a nearby retention pit 132 (i.e., a mud pit). While illustrated as being arranged at the outlet of the well bore 116 via the annulus 126, those skilled in the art will readily appreciate that the fluid processing unit(s) 128 may be arranged at any other location in the drilling assembly 100 to facilitate its proper function, without departing from the scope of the scope of the disclosure.

One or more additives may be added to the drilling fluid 122 and/or a well evaluation pill of the present disclosure via a mixing hopper 134 communicably coupled to or otherwise in fluid communication with a retention pit 132. The mixing hopper 134 may include, but is not limited to, mixers and related mixing equipment known to those skilled in the art.

In other embodiments, however, the additives may be added to the drilling fluid 122 and/or a well evaluation pills of the present disclosure at any other location in the drilling assembly 100. In at least one embodiment, for example, there could be more than one retention pit 132, such as multiple retention pits 132 in series. Moreover, the retention pit 132 may be representative of one or more fluid storage facilities and/or units where additives and/or the disclosed well evaluation pills of the present disclosure may be stored, reconditioned, and/or regulated until added to the drilling fluid 122 and/or introduced into the well bore.

As mentioned above, the disclosed well evaluation pills, methods, and systems may directly or indirectly affect the components and equipment of the drilling assembly 100. For example, the disclosed well evaluation pills, methods, and systems may directly or indirectly affect the fluid processing unit(s) 128 which may include, but is not limited to, one or more of a shaker (e.g., shale shaker), a centrifuge, a hydrocyclone, a separator (including magnetic and electrical separators), a desilter, a desander, a separator, a filter (e.g., diatomaceous earth filters), a heat exchanger, any fluid reclamation equipment, or the like. The fluid processing unit(s) 128 may further include one or more sensors, gauges, pumps, compressors, and the like used store, monitor, regulate, and/or recondition the well evaluation pill and/or other fluids.

The disclosed well evaluation pills, methods, and systems may directly or indirectly affect the pump 120, which representatively includes any conduits, pipelines, trucks, tubulars, and/or pipes used to fluidically convey the fluids and additives downhole, any pumps, compressors, or motors (e.g, topside or downhole) used to drive the fluids and/or well evaluation pills into motion, any valves or related joints used to regulate the pressure or flow rate of the fluids and additives, and any sensors (i.e., pressure, temperature, flow rate, etc.), gauges, and/or combinations thereof, and the like. The disclosed well evaluation pills, methods, and systems may also directly or indirectly affect the mixing hopper 134 and the retention pit 132 and their assorted variations.

The disclosed well evaluation pills, methods, and systems may also directly or indirectly affect the various downhole equipment and tools that may come into contact with the fluids and additives such as, but not limited to, the drill string 108, any floats, drill collars, mud motors, downhole motors and/or pumps associated with the drill string 108, and any MWD/LWD tools and related telemetry equipment, sensors or distributed sensors associated with the drill string 108. The disclosed well evaluation pills, methods, and systems may also directly or indirectly affect any downhole heat exchangers, valves and corresponding actuation devices, tool seals, packers and other well bore isolation devices or components, and the like associated with the well bore 116. The disclosed well evaluation pills, methods, and systems may also directly or indirectly affect the drill bit 114, which may include, but is not limited to, roller cone bits, PDC bits, natural diamond bits, any hole openers, reamers, coring bits, etc.

While not specifically illustrated herein, the disclosed well evaluation pills, methods, and systems may also directly or indirectly affect any transport or delivery equipment used to convey the fluids and additives to the drilling assembly 100 such as, for example, any transport vessels, conduits, pipelines, trucks, tubulars, and/or pipes used to fluidically move the fluids and/or well evaluation pills from one location to another, any pumps, compressors, or motors used to drive the fluids and additives into motion, any valves or related joints used to regulate the pressure or flow rate of the fluids and additives, and any sensors (i.e., pressure and temperature), gauges, and/or combinations thereof, and the like.

In one embodiment, the present disclosure provides a method comprising: introducing a well evaluation pill into a portion of a well bore penetrating a portion of a subterranean formation; allowing the well evaluation pill to interact with one or more components in the portion of the subterranean formation; detecting a change in the composition or properties of the well evaluation pill; and determining the presence of one or more components in the portion of the subterranean formation based at least in part on the detected change in the composition or properties of the well evaluation pill.

In another embodiment, the present disclosure provides a method comprising: using a well servicing fluid to perform an operation in at least a portion of a well bore penetrating a portion of a subterranean formation; introducing a well evaluation pill into the portion of the well bore penetrating the portion of the subterranean formation; allowing the well evaluation pill to interact with one or more components in the portion of the subterranean formation; circulating the well evaluation pill out of the well bore; detecting a change in the composition or properties of the well evaluation pill; determining the presence of one or more components in the portion of the subterranean formation based at least in part on the detected change in the composition or properties of the well evaluation pill.

In another embodiment, the present disclosure provides a system comprising: a gas extractor that removes a gas sample from a well evaluation pill that has been circulated in a well bore penetrating a portion of a subterranean formation; a gas analyzer that analyzes the gas sample from the well evaluation pill to determine at least one characteristic of the well evaluation pill; a central database and acquisition system that uploads data relating to at least one characteristic of the well evaluation pill from the gas analyzer; and a control system that uses the data relating to the characteristic of the well evaluation pill to detect a change in the composition or one or more properties of the well evaluation pill, and determine the presence of one or more components in the portion of the subterranean formation based at least in part on the detected change in the composition or one or more properties of the well evaluation pill.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b")

disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an", as used in the claims, are defined herein to mean one or more than one of the element that it introduces. If there is any conflict in the usages of a word or term in this specification and one or more patent or other documents that may be incorporated herein by reference, the definitions that are consistent with this specification should be adopted.

What is claimed is:

1. A method comprising:
   introducing a well evaluation pill into a portion of a well bore penetrating a portion of a subterranean formation;
   allowing the well evaluation pill to interact with one or more components in the portion of the subterranean formation;
   detecting a change in the composition or properties of the well evaluation pill;
   determining the presence of one or more components in the portion of the subterranean formation based at least in part on the detected change in the composition or properties of the well evaluation pill;
   determining an expected change in the composition or properties of the well evaluation pill based at least in part on an initial composition or property of the well evaluation pill and the estimated composition of the portion of the subterranean formation or a fluid residing therein;
   comparing the expected change in the composition or properties of the well evaluation pill with the detected change in the composition or properties of the well evaluation pill; and
   determining the presence of the one or more components in the portion of the subterranean formation based at least in part on the comparison of the expected change in the composition or properties of the well evaluation pill with the detected change in the composition or properties of the well evaluation pill.

2. The method of claim 1 wherein the density of the well evaluation pill is lower than the density of a fluid present in the well bore.

3. The method of claim 2 further comprising introducing an additional pill into the portion of the well bore penetrating the portion of the subterranean formation, wherein the density of the additional pill is higher than the density of the fluid present in the well bore.

4. The method of claim 1 wherein a well servicing fluid is present in the well bore.

5. The method of claim 1 wherein the well evaluation pill selectively reacts with, dissolves, absorbs, or captures one or more selected components in the formation.

6. The method of claim 1 wherein the composition of the well evaluation pill is formulated so that the well evaluation pill will alter one or more rheological properties of a fluid in the portion of the subterranean formation.

7. The method of claim 1 wherein the volume of the well evaluation pill is from about 50 bbl to about 100 bbl.

8. The method of claim 1 further comprising circulating at least a portion of the well evaluation pill out of the well bore.

9. The method of claim 1 further comprising accessing data regarding the composition or properties of the well evaluation pill from a remote location.

10. A method comprising:
    using a well servicing fluid to perform an operation in at least a portion of a well bore penetrating a portion of a subterranean formation;
    introducing a well evaluation pill into the portion of the well bore penetrating the portion of the subterranean formation;
    allowing the well evaluation pill to interact with one or more components in the portion of the subterranean formation;
    circulating the well evaluation pill out of the well bore;
    detecting a change in the composition or properties of the well evaluation pill;
    determining the presence of one or more components in the portion of the subterranean formation based at least in part on the detected change in the composition or properties of the well evaluation pill;
    determining an expected change in the composition or properties of the well evaluation pill based at least in part on an initial composition or property of the well evaluation pill and the estimated composition of the portion of the subterranean formation or a fluid residing therein;
    comparing the expected change in the composition or properties of the well evaluation pill with the detected change in the composition or properties of the well evaluation pill; and
    determining the presence of the one or more components in the portion of the subterranean formation based at least in part on the comparison of the expected change in the composition or properties of the well evaluation pill with the detected change in the composition or properties of the well evaluation pill.

11. The method of claim 10 wherein the density of the well evaluation pill is lower than the density of the well servicing fluid.

12. The method of claim 10 wherein the well evaluation pill selectively reacts with, dissolves, absorbs, or captures one or more selected components in the formation.

13. The method of claim 10 further comprising accessing data regarding the composition or properties of the well evaluation pill from a remote location.

14. The method of claim 10 wherein the operation comprises a cementing operation.

15. The method of claim 10 wherein the operation comprises a stimulation operation.

16. The method of claim 15 further comprising allowing the well evaluation pill to penetrate one or more fractures or voids in at least a portion of the subterranean formation that were created or enhanced during the stimulation operation.

17. The method of claim 10 wherein the well servicing fluid comprises a drilling fluid, and the operation comprises a drilling operation.

* * * * *